United States Patent [19]  
Urbach et al.

[11] Patent Number: 4,920,144  
[45] Date of Patent: Apr. 24, 1990

[54] DERIVATIVES OF BICYCLIC AMINO ACIDS, AGENTS CONTAINING THEM AND THEIR USE AS HYPOTENSIVES

[75] Inventors: Hansjörg Urbach, Kronberg/Taunus; Rainer Henning, Hattersheim am Main; Reinhard Becker, Wiesbaden, all of Fed. Rep. of Germany

[73] Assignee: Hoechst Aktiengesellschaft, Frankfurt am Main, Fed. Rep. of Germany

[21] Appl. No.: 332,338

[22] Filed: Apr. 3, 1989

Related U.S. Application Data

[63] Continuation of Ser. No. 865,479, May 21, 1986, abandoned.

[30] Foreign Application Priority Data

May 23, 1985 [DE] Fed. Rep. of Germany ....... 3518514

[51] Int. Cl.$^5$ .................. A61K 31/40; A61K 31/465; C07D 403/12; C07D 209/02
[52] U.S. Cl. ..................................... 514/412; 514/414
[58] Field of Search ............... 514/412, 414; 548/344, 548/452, 455

[56] References Cited

U.S. PATENT DOCUMENTS 4,562,202 12/1985 Urbach et al. .................. 514/423  
4,587,258 5/1986 Gold et al. ..................... 514/412

FOREIGN PATENT DOCUMENTS 135181 3/1985 European Pat. Off. .  
3210496 10/1983 Fed. Rep. of Germany .  
8600896 2/1986 PCT Int'l Appl. .  
83/1989 3/1983 South Africa .

Primary Examiner—David B. Springer  
Attorney, Agent, or Firm—Finnegan, Henderson, Farabow, Garrett and Dunner

[57] ABSTRACT

The invention relates to new derivatives of the bicyclic amino acids of the formula I

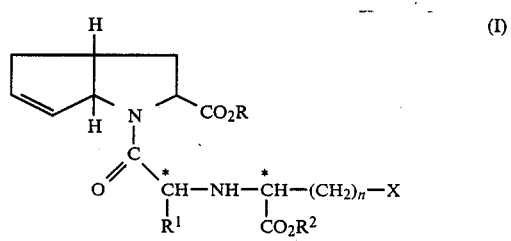

in which n denotes 0, 1 or 2, R denotes hydrogen, alkyl or aralkyl, $R^1$ denotes hydrogen or alkyl, alkenyl, cycloalkyl, cycloalkenyl, cycloalkylalkyl, optionally substituted aryl or partially hydrogenated aryl, aryl-($C_1$ to $C_4$)-alkyl or aroyl-$C_1$-alkyl, both of which can be substituted, a monocyclic or bicyclic heterocyclic radical or a side chain of a naturally occurring amino acid, $R^2$ denotes hydrogen, alkyl, alkenyl or aralkyl, X denotes alkyl, alkenyl, cycloalkyl or aryl which can be substituted, or 3-indolyl, and to their salts, to a process for their preparation, to agents containing them, and to their use.

12 Claims, No Drawings

DERIVATIVES OF BICYCLIC AMINO ACIDS, AGENTS CONTAINING THEM AND THEIR USE AS HYPOTENSIVES

This is a continuation of application Ser. No. 06/865,479, filed May 21, 1986, abandoned.

The invention relates to new derivatives of the bicyclic amino acids of the formula I

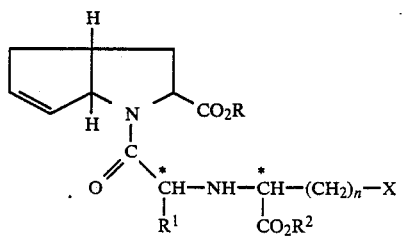

in which n denotes 0, 1 or 2,

R denotes hydrogen, ($C_1$ to $C_6$)-alkyl or aralkyl having 7 to 9 carbon atoms, $R^1$ denotes hydrogen or ($C_1$ to $C_6$)-alkyl which can optionally be substituted by amino, ($C_1$ to $C_4$)-acylamino or benzoylamino, ($C_2$ to $C_6$)-alkenyl, ($C_5$ to $C_9$)-cycloalkyl, ($C_5$ to $C_9$)-cycloalkenyl, ($C_5$ to $C_7$)-cycloalkyl-($C_1$ to $C_4$)-alkyl, aryl or partially hydrogenated aryl, each of which can be substituted by ($C_1$ to $C_4$)-alkyl, ($C_1$ or $C_2$)-alkoxy or halogen, aryl-($C_1$ to $C_4$)-alkyl or aroyl-$C_1$-alkyl, both of which can be substituted in the aryl radical as defined previously, a monocyclic or bicyclic heterocyclic radical having 5 to 7 or 8 to 10 ring atoms, 1 or 2 of these ring atoms being sulfur or oxygen atoms and/or 1 to 4 of these ring atoms being nitrogen atoms, or a side chain of a naturally occurring amino acid, $R^2$ denotes hydrogen, ($C_1$ to $C_6$)-alkyl, ($C_2$ to $C_6$)-alkenyl or aryl-($C_1$ to $C_4$)-alkyl, X denotes ($C_1$ to $C_6$)-alkyl, ($C_2$ to $C_6$)-alkenyl, ($C_5$ to $C_9$)-cycloalkyl, aryl which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkyl-amino or methylenedioxy, or 3-indolyl, and to their physiologically acceptable salts.

Particularly suitable salts are alkali metal or alkaline earth metal salts, salts with physiologically tolerated amines and salts with inorganic or organic acids such as, for example, HCl, HBr, $H_2SO_4$, maleic acid or fumaric acid.

In this context and in the following, aryl is to be understood to be optionally substituted phenyl or naphthyl. Alkyl can be straight-chain or branched.

In the preferred configuration of the hydrogen atoms at C-1 and C-5 of the bicycle, two possible configurations of the carboxyl group are suitable, namely the exo position (formula residue Ia) and the endo position (formula residue Ib) of the carboxyl group.

The endo position of the carboxyl group on C-3 is defined such that the carboxyl group faces in the direction of the unsaturated 5-membered ring of the bicycle, i.e. the concave side of the bicycle (formula residue Ib).

Correspondingly, the exo position of the carboxyl group on C-3 is defined such that the carboxyl group is oriented in the direction of the relevant bridgehead hydrogen atoms (formula residue Ia).

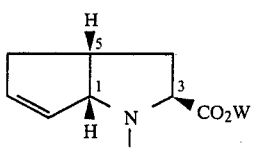

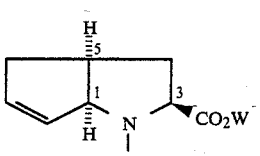

Compounds of the formula I have chiral carbon atoms in positions C-1, C-3, C-5 and in the carbon atoms of the side chain labeled with an asterisk. The invention relates to both the R- and the S-configuration at all centers. The compounds of the formula I can thus be in the form of optical isomers, diastereomers, racemates or mixtures thereof. However, preferred compounds of the formula I are those in which the carbon atom 3 in the bicyclic ring system, and the carbon atoms of the side chain labeled with an asterisk (*), have the S-configuration.

Particularly preferred compounds of the formula I are those in which n denotes 2, R denotes hydrogen or alkyl having 1 to 4 carbon atoms, $R^1$ denotes hydrogen, ($C_1$ to $C_3$)-alkyl, ($C_2$ or $C_3$)-alkenyl, benzyl, phenethyl, 4-aminobutyl or benzoylmethyl, $R^2$ denotes hydrogen, ($C_1$ to $C_4$)-alkyl or benzyl and X denotes methyl, cyclohexyl, phenyl which can be monosubstituted or disubstituted or, in the case of methoxy, trisubstituted by ($C_1$ or $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)alkylamino, nitro or methylenedioxy, in particular those compounds of the formula I in which n denotes 2, R denotes hydrogen, $R^1$ denotes methyl, X denotes phenyl, methyl or cyclohexyl, $R^2$ denotes hydrogen or ethyl, the bicycle has the cis-configuration, the carboxyl group is exo or endo-oriented, and the chiral carbon atoms which are identified by an asterisk (*) and carbon atom 3 have the S-configuration.

The invention also relates to a process for the preparation of the compounds of the formula I. One process variant comprises reaction of a compound of the formula II

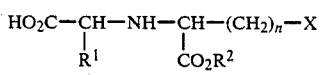

in which n, $R^1$, $R^2$ and X have the meanings as in formula I, with a compound of the formula III

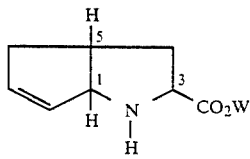
(III)

in which

W denotes hydrogen or a radical which can be eliminated with acid or base, in particular a tert.-butyl radical, by known amide-forming methods of peptide chemistry and, where appropriate, then elimination of the radical W by acid treatment and, where appropriate, also of the radical $R^2$ by additional acid or base treatment, in each case the free carboxylic acids being obtained.

Furthermore, compounds of the formula I can also be prepared in such a manner that a compound of the formula IV

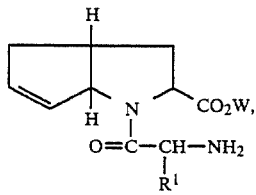
(IV)

in which $R^1$ has the meaning as in formula I, and W has the meaning as in formula III, is reacted by the procedure described in J. Amer. Chem. Soc. 93, 2897 (1971) with a compound of the formula V

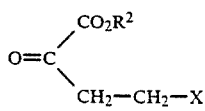
(V)

in which $R^2$ and X have the meanings as in formula I, and the resulting Schiff's bases are reduced and then, where appropriate, the radical W and/or the radical $R^2$ are eliminated as described above, with formation of the free carboxyl groups. The reduction of the Schiff's bases can be carried out by electrolysis or with reducing agents such as, for example, sodium borohydride or sodium cyanoborohydride.

Compounds of the formula I in which R represents hydrogen can, where appropriate, be converted by methods known per se into their esters of the formula I in which R denotes ($C_1$ to $C_6$)-alkyl or ($C_7$–$C_9$)-aralkyl.

The invention also relates to compounds of the formula III

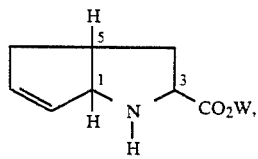
(III)

in which the hydrogen atoms on the carbon atoms 1 and 5 have the cis-configuration with respect to one another, and the group —$CO_2W$ on carbon atom 3 is oriented exo or endo with respect to the bicyclic ring system, and in which W denotes hydrogen or a radical which can be eliminated with acid.

These compounds are used, according to the invention, as starting materials for the synthesis of compounds of the formula I and can, according to the invention, be prepared by the following procedure:

Compounds of the formula (VI) and (VII),

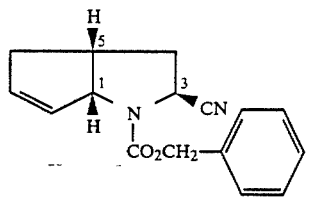
(VI)

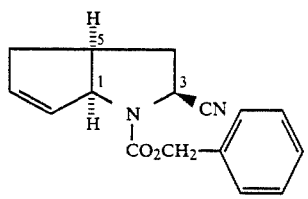
(VII)

in which the hydrogen atoms on carbon atoms 1 and 5 have the cis-configuration with respect to one another, and the nitrile group on carbon atom 3 is in the exo-position in the compound of the formula (VI) and in the endo-position in the compound of the formula (VII), are described in the literature (D. A. Evans et al., Tetrahedron Letters Vol. 26, 1907 (1985)). These compounds are hydrolyzed under acid or alkaline conditions to give compounds of the formula III in which W denotes hydrogen.

Thus, for example, the compound of the formula VI is advantageously hydrolyzed with concentrated hydrobromic acid under reflux to give the compound of the formula (IIIa),

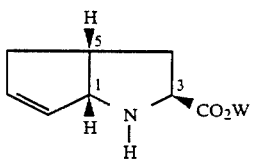
(IIIa)

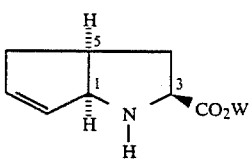
(IIIb)

in which W denotes hydrogen, the hydrogen atoms on carbon atoms 1 and 5 have the cis-configuration with respect to one another, and the $CO_2W$ group on carbon atoms 3 is in the exo position with respect to the olefinic 5-membered ring. Correspondingly, the compound VII results in the compound of the formula IIIb in which W denotes hydrogen, the hydrogen atoms on carbon atoms 1 and 5 have the cis-configuration with respect to one another, and the $CO_2W$ group on carbon atom 3 is in the endo position with respect to the olefinic 5-membered ring.

The hydrolysis can also be carried out with hydrochloric acid which is concentrated or diluted with water or alcohol. Dilute sulfuric acid can also be used.

The hydrolysis under basic conditions is preferably carried out with aqueous or alcoholic/aqueous sodium hydroxide solution or potassium hydroxide solution.

It is possible to prepare in an analogous manner, by the preparation procedure of Tetrahedron Letters Publication 26, 1907 (1985) further N-acyl derivatives of the formula VIa and VIIa in which $R^3$ represents $(C_1-C_6)$-alkyl, $(C_5-C_9)$-cycloalkyl, $(C_2-C_6)$-alkenyl, $(C_1-C_6)$-alkoxy, aryl, aryloxy, aryl-$(C_1-C_4)$-alkyl or aryl-$(C_1-C_4)$-alkoxy, which can be hydrolyzed under basic or acid conditions to give compounds of the formula IIIa and IIIb in which W denotes hydrogen.

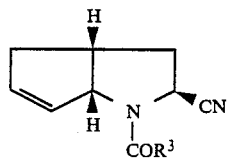
(VIa)

Thus, for example, it is possible to prepare the N-tert.-butoxycarbonyl compounds of the formula VIa and VIIa ($R^3 = -O-C(CH_3)_3$), which are hydrolyzed under acid conditions (for example with concentrated hydrobromic acid) to give compounds of the formula IIIa and IIIb with W=hydrogen.

The endo-cis compounds IIIb and the exo-cis compounds IIIa are each in the form of racemates. The amino acids may, where appropriate, be esterified. The preferred tert.-butyl esters of the amino acids of the formula III (W=tert.-butyl) are obtained by methods customary in peptide chemistry, such as, for example, by reaction of the acids with isobutylene in an inert organic solvent (for example dioxane) in the presence of acids (such as, for example, sulfuric acid). The following process has proved to be particularly advantageous:

The appropriate amino acid is actylated on nitrogen with a group which can be eliminated with base, such as, for example, the methylsulfonylethoxycarbonyl group (=MSC), (Tesser, Balvert-Geers, Int. J. Pept. Protein Res. 7, 295 (1975)) or the 9-fluorenylmethyloxycarbonyl group (=FMOC).

The carboxylic acid is reacted, in the neutral or weakly basic pH range, with tert.-butanol in an organic solvent such as, for example, pyridine, in the presence of N-propylphosphonic anhydride, to give the corresponding tert.-butyl ester. The tert.-butyl ester can also be obtained by reaction of, for example, the FMOC-carboxylic acid derivative with tert.-butanol in the presence of phosphorus oxychloride. The tert.-butyl ester of the formula III (W=tert.-butyl) is obtained by elimination of the MSC or FMOC protective group in the strongly alkaline pH range using alkali in an aqueous solvent or an organic base in an organic solvent.

The compounds of the formula II with n=2, $R^1$=methyl and $R^2$=methyl or ethyl, and X=phenyl, which are used as starting materials for the preparation of the compounds of the formula I, are known (European Patent Application No. 37,231). Likewise, compounds of the formula II with n=2, $R^1$ and X=$CH_3$, and $R^2=C_2H_5$ are known (Tetrahedr. Lett. 23, (1982), 1677). The compounds of the formula II can be prepared by a variety of procedures. One synthesis variant starts from a ketone of the formula VIII, mentioned below, which is reacted, by known procedures in a Mannich reaction, with a compound of the formula IX, mentioned below, together with amino acid esters of the formula X

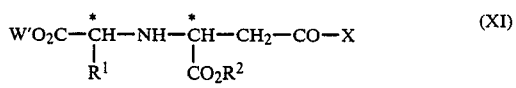

in which $R^1$ has the abovementioned meaning, and W' denotes a radical which can be eliminated by hydrogenolysis or with acid, in particular a benzyl or a tert.-butyl radical, to give a compound of the formula XI in which $R^1$, $R^2$, X and W' have the abovementioned meanings, with the proviso that when W' denotes a radical which can be eliminated by hydrogenolysis, in particular benzyl, $R^2$ may not have the meaning of W'. When the radical W' is eliminated by hydrogenolysis using, for example, palladium, on uptake of 3 mol-equivalents of hydrogen compounds of the formula II are obtained.

Compounds of the formula XI can also be obtained by known procedures by Michael addition of a compound of the formula XII

with a compound of the abovementioned formula X. This process is preferably suitable for the preparation of those compounds of the formula XI in which $R^1$ denotes methyl, $R^2$ denotes ethyl and X denotes aryl.

The compounds of the formula XI are obtained as mixtures of diastereomers. Preferred diastereomers of the formula XI are those in which the chiral carbon atoms labeled with an asterisk each have a S-configuration. These can be separated off by, for example, crystallization or by chromatography on, for example, silica gel. The configuration of the chiral carbon atoms is retained during the subsequent elimination of the radical W'.

The compounds of the abovementioned formula IV which are used as starting materials for the preparation of the compounds of the formula I are obtained by known procedures from the compounds of the abovementioned formula III by reaction with an N-protected 2-aminocarboxylic acid of the formula XIII

in which V denotes a protective group, and $R^1$ has the abovementioned meaning. A suitable protective group V, which is eliminated again after reaction is complete, is, for example, tert.-butoxycarbonyl.

The reaction of a compound of the formula II with a compound of the formula III to prepare a compound of the formula I is carried out by a condensation reaction known in peptide chemistry, the condensing agent added being, for example, dicyclohexylcarbodiimide and 1-hydroxybenzotriazole or n-propanephosphonic anhydride or methylethylphosphinic anhydride. The acids preferably used for the subsequent acid elimination of the radical W are trifluoroacetic acid or hydrogen chloride.

In the abovementioned reaction for the preparation of the compounds of the formulae III, IV and I, in each case the configurations of the intermediates at the bridgehead carbon atoms 1 and 5 are retained.

The compounds of the formula III are obtained as racemic mixtures and can be used as such in the further syntheses described above. However, they can also be used as the pure enantiomers after separation of the racemates into the optical antipodes using customary methods, for example via salt formation with optically active bases or acids. The pure enantiomers can also be obtained. If the compounds of the formula I are obtained as racemates, these can also be resolved into their enantiomers by the customary methods such as, for example, via salt formation with optically active bases or acids, or can be separated by chromatography.

When R is hydrogen, the compounds of the formula I according to the invention are in the form of internal salts. Since they are amphoteric compounds they are able to form salts with acids or bases. These salts are prepared in a customary manner by reaction with one equivalent of acid or base.

The compounds of the formula I and their salts have a longlasting and strong hypotensive action. They are potent inhibitors of angiotensin converting enzyme (ACE inhibitors). They can be used to control hypertension of various etiologies. It is also possible to combine them with other compounds having hypotensive, vasodilating or diuretic activity. Typical representatives of these classes of active compound are described in, for example, Erhardt-Ruschig, Arzneimittel (Drugs), 2nd edition, Weinheim, 1972. The compounds of the formula I can also be used to control coronary heart failure of a variety of etiologies. Administration can be intravenous, subcutaneous or oral.

The dose on oral administration is 1–100 mg, preferably 1–40 mg, per single dose for a patient of normal weight. It may also be raised in serious cases, since no toxic properties have hitherto been observed. It is also possible to reduce the dose, and this is particularly appropriate when diuretics are administered concurrently.

The compounds according to the invention can, in appropriate pharmaceutical formulation, be administered orally or parenterally. For an oral administration form, the active compounds are mixed with the additives customary for this purpose, such as vehicles, stabilizers or inert diluents, and converted by customary methods into suitable administration forms such as tablets, coated tablets, hard gelatine capsules, aqueous, alcoholic or oily suspensions or aqueous, alcoholic or oily solutions. Examples of inert vehicles which can be used are gum arabic, magnesium carbonate, potassium phosphate, lactose, glucose, magnesium stearyl fumarate or starch, in particular corn starch. This formulation can be carried out either as dry or moist granules. Examples of suitable oily vehicles or solvents are vegetable or animal oils, such as sunflower oil and fish liver oil.

For subcutaneous or intravenous administration, the active compounds or their physiologically tolerated salts are converted into solutions, suspensions or emulsions, if desired with the substances customary for this purpose, such as solubilizers, emulsifiers or other auxiliaries. Examples of suitable solvents for the new active compounds and the corresponding physiologically tolerated salts are: water, physiological saline solutions or alcohols, for example ethanol, propanediol or glycerol, in addition also sugar solutions such as glucose or mannitol solutions, as well as a mixture of the various solvents mentioned.

Unless otherwise indicated, the $^1$H-NMR data indicated in the examples which follow were determined in $CDCl_3$ and are indicated in δ (ppm).

EXAMPLE 1

2-[N-[(S)-1-Ethoxycarbonyl-3-phenylpropyl]-L-alanyl]-(1S,3S,5S)-2-azabicyclo[3.3.0]-7-octene-3-carboxylic acid (a)
1SR,3SR,5SR-2-Azabicyclo[3.3.0]-7-octene-3-carboxylic acid
(cis-endo-2-azabicyclo[3.3.30]-7-octene-3-carboxylic acid 1 g of N-benzyloxycarbonyl-1SR,3SR,5SR-2-azabicyclo[3.3.0]-7-octene-3-carbonitrile is heated with 10 ml of concentrated hydrobromic acid at 60°–70° C. After hydrolysis is complete, the mixture is evaporated in vacuo and then evaporated twice with toluene on a ®Rotavapor. The residue is taken up in water and the pH is adjusted to 4 with an ion exchanger (for example IRA 93). After removal of the ion exchanger, the aqueous solution is evaporated and the residue is purified on silica gel using methylene chloride/methanol/glacial acetic acid/water (20:10:0.5:0.5) or ethyl acetate/methanol 1:1, then methanol.

Yield: 0.4 g, melting point 254°–256° C. (decomposition), $R_f$: 0.05 ($SiO_2$; ethyl acetate, methanol 1:1) $^1$H-NMR (270 MHz, $D_2O$; ppm): 1,8–2.0 (m, 1H); 2.2–2.4 (m, 1H); 2.1–2.3 (m, 2H); 3.1–3.25 (m, 1H); 4.1–4.2 (dd, 1H); 4.8–4.9 (m, 1H); 5.8 (m, 1H); 6.1 (m, 1H).

(b)
N-Fluorenylmethyloxycarbonyl-1SR,3SR,5SR-2-azabicyclo[3.3.0]-7-octene-3-carboxylic acid 1.5 g of acid from Example 1 a is dissolved in 22 ml of water/dioxane (1:1), and 1.5 g of $NaHCO_3$ and 3.7 g of 9-fluorenyl-methyl succinimidyl carbonate (FMOC-ONSuc) are added. The mixture is stirred at room temperature for 2 days. The temperature can be raised to 35° C. to increase the rate of reaction. After the reaction, the dioxane is removed in vacuo, and the aqueous solution is acidified to pH 3.5, extracted with ethyl acetate, and the ethyl acetate solution is dried and evaporated in vacuo.

Yield: 3.2 g, $R_f$: 0.64 ($SiO_2$; ethyl acetate/methanol 1:1, $I_2$)

$^1$H-NMR (270 MHz, $CD_3OD$; ppm): 1.6–3.0 (m, 5H); 4.0–4.9 (m, 5H); 5.45–6.0 (m, 2H); 7.25–7.9 (m, 8H).

($c_1$) Tert.-butyl
N-fluorenylmethyloxycarbonyl-1SR,3SR,5SR-2-azabicyclo[3.3.0]-7-octene-3-carboxylate 8 ml of pyridine and 20 ml of tert.-butanol are added to 3.0 g of acid from Example 1 b, at −10° C., and then 0.85 ml of phosphorus oxychloride is added. After 30 min, the cooling is removed and the mixture is stirred at room temperature and then at 30° C. After the reaction, the mixture is poured onto aqueous sodium bicarbonate solution, extraction is carried out with ethyl acetate, and the extract is dried and then evaporated in vacuo. The residue is chromatographed on $SiO_2$ using cyclohexane/ethyl acetate 4:1.

Yield: 1.2 g

R$_f$: 0.6 (SiO$_2$; cyclohexane/ethyl acetate 1:1; I$_2$ staining)

(c$_2$)

10 ml of isobutylene are condensed, 270 mg of the compound from Example (1b) dissolved in 2 ml of methylene chloride, are added, and 0.1 ml of concentrated sulfuric acid is added to the mixture. It is left in an autoclave at room temperature and under a pressure of 10 bar of nitrogen for 48 hours. After the reaction, the mixture is taken up in methylene chloride, 5% strength aqueous Na$_2$CO$_3$ solution is added, and the methylene chloride phase is evaporated in vacuo. The residue is deluted with a small quantity of water, the aqueous solution is extracted with ethyl acetate, and the organic phase is dried over MgSO$_4$ and is, after filtration, evaporated in vacuo. The residue is purified on silica gel using cyclohexane acetate 85:15.

Yield: 170 mg; R$_f$: 0.78 (SiO$_2$; methylene chloride/methanol 4:1, I$_2$)

$^1$H-NMR (CDCl$_3$; ppm): 1.35 (m, 9H); 1.8 (m, 1H); 2.1 (m, 1H); 2.45 (m, 2H); 2.82 (m, 1H); 4.18 (m, 2H); 4.37 (m, 2H); 4.7+4.9 (je d, 1H); 5.65+5.95 (je d, 2H); 7.2–7.7 (m, 8H).

(d) Tert.-butyl 1SR,3SR,5SR,-2-azabicyclo[3.3.0]-7-octene-3-carboxylate 3 g of the tert.-butyl ester from Example 1 c are stirred in 60 ml of ≈2.5 n diethylamine in dimethylformamide at room temperature for one hour. After the reaction is complete (TLC check), the mixture is evaporated under high vacuum, and the residue is triturated with diisopropyl ether.

The residue is chromatographed on SiO$_2$ using ethyl acetate/cyclohexane 1:1 as a eluent.

Yield: 0.7 g of tert.-butyl ester (m/e: 209)

$^1$H-NMR (270 MHz, CDCl$_3$; ppm): 1.4–1.6 (m, 11H); 2.25–2.9 (m, 3H); 3.6 (dd, 1H); 4.25–4.35 (m, 1H); 5.6–5.75 (m, 2H).

(e) Tert.-butyl 2-[N-[(S)-1-ethoxycarbonyl-3-phenylpropyl]-L-alanyl]-(1SR,3SR,5SR)-2-azabicyclo[3.3.0]-7-octene-3-carboxylate 0.28 g of N-(1-S-carbethoxy-3-phenylpropyl)-S-alanine is dissolved in 4 ml of dimethylformamide. At room temperature, 0.15 g of hydroxybenzotriazole and 0.22 g of dicyclohexylcarbodiimide are added. The mixture is stirred at room temperature for 4 hours. Then 0.24 g of tert.-butyl ester from Example 1 d is added, and the mixture is stirred at room temperature for 20 hours. It is diluted with diethyl acetate, the urea is filtered off with suction, and the filtrate is evaporated in vacuo. The residue is taken up in ethyl acetate, and the ethyl acetate solution is washed with bicarbonate solution, dried and evaporated. Yield: 0.4 g of oil (m/e: 470)

(f) Tert.-butyl 2-[N-[(S)-1-ethoxycarbonyl-3-phenylpropyl]-L-alanyl]-(1S,3S,5S)-2-azabicyclo[3.3.0]-7-octene-3-carboxylate The oily residue from Example 1 e (0.4 g) is separated into the diastereomers on silica gel using ethyl acetate/cyclohexane 2:1 or petroleum ether/acetone 2:1, respectively, as the eluting agent. 0.15 g of the tert.-butyl ester with the 3-S-endo configuration is obtained.

R$_f$: 0.43; m/e 470; [α]$_D^{20}$: +23.4 (c=3, CHCl$_3$).

$^1$H-NMR data (270 MHz, CDCl$_3$; ppm): 1.4 (s, 9H); 0.8–3.8 (m, 18H); 4.0–4.6 (m, 2H); 4.9–5.2 (m, 1H); 5.4–6.0 (m, 2H); 7.1–7.3 (m, 5H).

The corresponding R,R,R,S,S isomer shows [α]$_D^{20}$: −51.4° (c=5, CHCl$_3$).

(g) 2-[N-[(S)-1-Ethoxycarbonyl-3-phenylpropyl]-L-alanyl]-(1SR,3SR,5SR)-2-azabicyclo[3.3.0]-7-octene-3-carboxylic acid 0.15 g of the tert.-butyl ester from Example 1 e is dissolved in 1 ml of trifluoroacetic acid at 0° C., and the solution is stirred at this temperature for 3 hours. The trifluoroacetic acid is evaporated off in vacuo, and the residue is crystallized from diisopropyl ether.

Yield of trifluoroacetate: 0.08 g

The trifluoroacetate is converted into the amino acid using a basic ion exchanger (OH$^-$ form) in methanol/water 60:40.

Yield: 0.6 g (m/e: 486; after silylation)

(h) 2-[N-[(S)-1-Ethoxycarbonyl-3-phenylpropyl[-L-alanyl]-(1S,3S,5S)-2-azabicyclo[3.3.0]-7-octene-3-carboxylic acid A solution of 0.5 g of the tert.-butyl ester from Example 1 f in 5 ml of methylene chloride is saturated with dry hydrogen chloride gas, and the solution is allowed to stand at 20°–25° C. for 16 hours. The solution is evaporated in vacuo. The residue is triturated with diisopropyl ether and filtered off with suction.

Yield: 0.4 g

The hydrochloride is converted into the betaine using a basic ion exchanger (®Amberlite 7RA93) at pH 4.0–4.5.

Yield: 0.3 g (m/e: 486 after silylation)

$^1$H-NMR (270 MHz, CDCl$_3$; ppm): 0.8–1.5 (m, 6H); 1.7–3.2 (m, 9H); 3.6–5.2 (m, 6H); 5.6–6.1 (m, 2H); 7.1–7.3 (m, 5H).

The corresponding R,R,R,S,S isomer shows [α]$_D^{20}$: −38.3° (c=3.5, CHCl$_3$).

EXAMPLE 2

2-[N-[(S)-1-Ethoxycarbonyl-3-phenylpropyl]-L-alanyl]-(1R,3S,5R)-2-azabicyclo[3.3.0]-7-octene-3-carboxylic acid

(a) 1RS,3SR,5RS-2-Azabicyclo[3.3.0]-7-octene-3-carboxylic acid (cis-exo-2-azabicyclo[3.3.0]-7-octene-3-carboxylic acid)

1 g of N-benzyloxycarbonyl-1RS,3SR,5RS-2-azabicyclo[3.3.0]-7-octene-3-carbononitrile is hydrolyzed in analogy to Example 1 a.

Yield: 0.5 g $^1$H-NMR (270 MHz, D$_2$O; ppm): 2.1 (m, 1H); 2.4 (m, 2H); 2.8 (m, 1H); 3.18 (m, 1H); 4.05 (dd, 1H); 4.92 (broad d, 1H); 5.75 (m, 1H); 6.23 (m. 1H).

(b) N-Fluorenylmethyloxycarbonyl-1RS,3SR,5RS-2-azabicyclo[3.3.0]-7-octene-3-carboxylic acid 1.5 g of acid from Example 2 are reacted in analogy to Example 1 b.

Yield: 3.0 g; R$_f$=0.54 (SiO$_2$; ethyl acetate/methanol 1:1; I$_2$)

(c) Tert.-butyl
N-fluorenylmethyloxycarbonyl-1RS,3SR,5RS-2-azabicyclo[3.3.0]-7-octene-3-carboxylate 3.0 g of acid from Example 2 b are reacted in analogy to Example 1 (c2).

Yield: 1.8 g (m/e: 431)

$^1$H-NMR (270 MHz, CDCl$_3$; ppm): 1.45 (d, 9H); 1.87 (m, 1H); 2.2 (m, 2H); 2.55 (m, 1H); 2.9 (m, 1H); 4.15–4.6 (m, 4H); 4.82+5.0 (each d, 1H); 5.65+6.0 (each m, 2H); 7.25–7.8 (m, 8H).

(d) Tert.-butyl
1RS,3SR,5RS-2-azabicyclo[3.3.0]-7-octene-3-carboxylate 3 g of the tert.-butyl ester from Example 2c are reacted in analogy to the process described in Example 1 d.

Yield: 1.1 g (m/e: 209)

$^1$H-NMR (270 MHz, CDCl$_3$; ppm): 1.45 (s, 9H); 1.8–2.0 (m, 2H); 2.1–2.2 (m, 1H); 2.88 (s, 1H); 2.53–2.68 (m, 1H); 2.7–2.9 (m, 1H); 3.5–3.58 (dd, 1H); 4.52 (m, 1H); 5.57 (m, 1H); 5.72 (m, 1H).

(e) Tert.-butyl
2-[N-[(S)-1-ethoxycarbonyl-3-phenylpropyl]-L-alanyl]-(1R,3S,5R)-2-azabicyclo[3.3.0]-7-octene-3-carboxylate 0.3 g of the tert.-butyl ester from Example 2 d is reacted in analogy to Examples 1 e and 1 f.

Yield: 0.25 g; $[\alpha]_D^{20}$: −98° (c=1, CH$_3$=H).

$^1$H-NMR (270 MHz, CDCl$_3$; ppm): 1.45 (s, 9H); 1.2–3.7 (m, 18H); 4.0–5.1 (m, 4H); 5.65–6.0 (m, 2H); 7.1–7.3 (m, 5H).

The isomeric compound tert.-butyl 2-[N-[(S)-1-ethoxy-carbonyl-3-phenylpropyl)-L-alanyl]-(1S,3R,5S)-2-azabicyclo[3.3.0]-7-octene-3-carboxylate shows $[\alpha]_D^{20}$: +86.4° (c=1, CH$_3$OH).

(f)
2-[N-[(S)-1-Ethoxycarbonyl-3-phenylpropyl]-L-alanyl]-(1R,3S,5R)-2-azabicyclo[3.3.0]-7-octene-3-carboxylic acid This compound is prepared from 0.4 g of the tert.-butyl ester of Example 2 e in analogy to the process described in Example 1 h.

Yield: 0.25 g (m/e: 486 after silylation); $[\alpha]_D^{20}$: −161,8° (c=1.5, CH$_3$OH).

$^1$H-NMR (270 MHz, DMSO-d$_6$; ppm): 1.0–1.3 (m, 6H); 1.6–3.73 (m, 9H); 4.0–4.15 (m, 3H); 4.3 (d, 1H); 4.8 (broad t, 1H); 5.7 (m, 1H); 5.84 (m, 1H); 7.1–7.3 (m, 5H).

The isomeric compound 2-[N-[(S)-1-ethoxycarbonyl-3-phenylpropyl]-L-alanyl]-(1S,3R,5S)-2-azabicyclo[3.3.0]-7-octene-3-carboxylic acid shows $[\alpha]_D^{20}$: +110.3° (c=2.5, CH$_3$OH).

EXAMPLE 3

2-[N-[(S)-1-Carboxy-3-phenylpropyl]-L-alanyl]-(1SR,3SR,5SR)-2-azabicyclo[3.3.0]-7-octene-3-carboxylic acid One equivalent of potassium hydroxide and a 10% excess of 4N potassium hydroxide solution are added to a solution in 2 ml of water of 0.1 g of the ethyl ester prepared in Example 1 g. After the reaction solution has been stirred at 20° to 25° C. for 4 hours, the pH is adjusted to 4 with 2N hydrochloric acid, and the mixture is evaporated in vacuo. The residue is taken up in ethyl acetate, and the precipitated salt is filtered off. The ethyl acetate solution is evaporated, and the residue is triturated with diisopropyl ether and filtered off with suction.

Yield: 0.08 g $^1$H-NMR data: (after H/D exchange) 1.1 (d, 3H); 1.0–3.8 (m, 9H); 3.9–4.8 (m, 4H); 5.6–6.0 (m, 2H); 7.1–7.3 (m, 5H)

EXAMPLE 4

2-[N-[(S)-1-Carboxy-3-phenylpropyl]-L-alanyl]-(1S,3S,5S)-2-azabicyclo[3.3.0]-7-octene-3-carboxylic acid 0.1 g of ethyl ester from Example 1 h is reacted in analogy to Example 3.

Yield: 0.08 g (m/e 386=MW—H$_2$O)

$^1$H-NMR (DMSO-d$_6$; ppm): 1.2 (d, 3H); 1.7–3.3 (m, 9H); 3.6–5.2 (m, 4H); 5.6–6.0 (m, 2H); 7.1–7.3 (m, 5H).

EXAMPLE 5

2-[N-[(S)-1-Carboxy-3-phenylpropyl]-L-alanyl]-(1R,3S,5R)-2-azabicyclo[3.3.0]-7-octene-3-carboxylic acid 0.1 g of ethyl ester from Example 2 f is reacted in analogy to Example 3.

Yield: 0.07 g (m/e: 368=MW—H$_2$O)

$^1$H-NMR (DMSO-d$_6$; ppm): 1.1 (d, 3H); 1.5–3.5 (m, 9H); 3.7–5.2 (m, 4H); 5.6–6.1 (m, 2H); 7.1–7.3 (m, 5H).

EXAMPLE 6

2-[Nα-[(S)-1-Ethoxycarbonyl-3-phenylpropyl]-L-lysyl]-(1S,3S,5S)-2-azabicyclo[3.3.0]-7-octene-3-carboxylic acid dihydrochloride (a)
Nα-[(S)-1-Ethoxycarbonyl-3-phenylpropyl]-Nε-tert.-butoxycarbonyl-L-lysine 0.42 g (0.0002 mol) of ethyl D-2-hydroxy-4-phenylbutyrate and 0.16 ml of dry pyridine are dissolved in 10 ml of dry methylene chloride, and the solution is cooled to 0° C. and 0.62 g of trifluoromethanesulfonic anhydride in 3 ml of absolute methylene chloride is added. The mixture is then stirred at room temperature for 2 hours. The solution is washed with water, dried and evaporated in vacuo. The residue is dissolved in 5 ml of dry methylene chloride, and the solution is added dropwise to a solution of the benzyl ester of Nε-tert.-butoxycarbonyl-L-lysine and 0.27 ml of triethylamine in 10 ml of dry methylene chloride. The mixture is stirred at room temperature for 2 hours. It is then washed with water, and the methylene chloride solution is dried over MgSO$_4$ and then, after removal of the MgSO$_4$, evaporated in vacuo. The residue is taken up in ethanol and hydrogenated with Pd/C under atmospheric pressure. After removal of the catalyst by filtration with suction, the solution is evaporated in vacuo.

Yield: 0.6 g $^1$H-NMR (D$_2$O)

1.4 (s, 9H);
1.0–1.4 (tr, 3H);
1.0–2.5 (m, 9H);
2.5–4.4 (m, 9H);
3.9–4.4 (g, 2H);
4.6–5.0 (m, 1H);
7.1–7.3 (m, 5H).

(b) Tert.-butyl 2-[Nα-[(S)-1-ethoxycarbonyl-3-phenylpropyl]-Nε-tert.-butoxycarbonyl-L-lysyl]-(1S,3S,5S)-2-azabicyclo[3.3.0]-7-octene-3-carboxylate 0.6 g of the acid from Example 6 a, 1 equivalent of the tert.-butyl ester from Example 1 d, and 4 equivalents of triethylamine are dissolved in 10 ml of methylene chloride. While cooling in ice, 0.9 ml of a 50% strength solution of n-propanephosphonic anhydride in methylene chloride is added, and the mixture is allowed to stand overnight at room temperature. It is washed successively with water, aqueous $KHSO_4$ solution, saturated $NaHCO_3$ solution and water.

The solution is then dried and evaporated in vacuo.

Yield: 0.9 g of two diastereomeric compounds as an oil.

The mixture of diastereomers is separated by column chromatography on silica gel using cyclohexane/ethyl acetate 2:1. The isomer which is eluted first is the abovementioned compound. 0.4 g of oil is obtained. (m/e: 627)

(c) 2-[Nα-[(S)-1-Ethoxycarbonyl-3-phenylpropyl]-L-lysyl]-(1S,3S,5S)-2-azabicyclo[3.3.0]-7-octene-3-carboxylic acid dihydrochloride 0.3 g of the compound obtained in Example 6 b is reacted in analogy to Example 1 h.

Yield: 0.15 g $^1$H-NMR (after H/D exchange):
0.9–2.5 (m, 18H);
2.6–4.6 (m, 8H);
4.6–5.1 (m, 2H);
7.2 (m, 5H).

EXAMPLE 7

2-[Nα-[(S)-1-Carboxy-3-phenylpropyl]-L-lysyl]-(1S,3S,5S)-2-azabicyclo[3.3.0]-7-octene-3-carboxylic acid 0.1 g of the compound obtained in Example 6 c is reacted in analogy to Example 3.

Yield: 0.08 g (m/e: 425; MW—$H_2O$)

EXAMPLE 8

2-[N-[(S)-1-Ethoxycarbonylbutyl]-L-alanyl]-(1SR,3SR,5SR)-2-azabicyclo[3.3.0]-7-octene-3-carboxylic acid hydrochloride

(a) Tert.-butyl 2-[N-[(S)-1-ethoxycarbonylbutyl]-L-alanyl]-(1SR,3SR,5SR)-2-azabicyclo[3.3.0]-7-octene-3-carboxylate 2.9 g of N-[(S)-1-ethoxycarbonylbutyl]-L-alanine (Tetrahedron Letters 23, 1677 (1982)) and 1 equivalent of tert.-butyl (1SR,3SR,5SR)-2-azabicyclo[3.3.0]-7-octene-3-carboxylate from Example 1 d are dissolved in 60 ml of dry methylene chloride. While cooling in ice, 5.5 ml of triethylamine are added dropwise. Then 6.7 ml of a 50% strength solution of n-propanephosphonic anhydride in methylene chloride are added. The mixture is stirred at 0° C. for 1 hour and at room temperature for a further 14 hours. Working up is carried out as described in Example 6 b.

Yield: 5.0 g of oil $^1$H-NMR
0.9 (t, 3H);
1.25 (t, 3H);
1.4 (s, 9H);
0.9–3.8 (m, 12H);
3.9–4.7 (m, 5H);
5.4–6.2 (m, 2H).

The residue comprises a mixture of the diastereomers tert.-butyl 2-[N-[(S)-1-ethoxycarbonylbutyl]-L-alanyl]-(1S,3S,5S)-2-azabicyclo[3.3.0]-7-octene-3-carboxylate and tert.-butyl 2-[N-[(S)-1-ethoxycarbonylbutyl]-L-alanyl]-(1R,3R,5R)-2-azabicyclo[3.3.0]-7-octene-3-carboxylate, which can be separated on silica gel using the solvent mixture cyclohexane/ethyl acetate 1:1.

(b) 2-[N-[(S)-1-Ethoxycarbonylbutyl]-L-alanyl]-(1SR,3SR,5SR)-2-azabicyclo[3.3.0]-7-octene-3-carboxylic acid hydrochloride 1.0 g of the residue from Example 8 a is reacted as described in Example 1 h.

Yield. 0.8 g (m/e: 352)

EXAMPLE 9

2-[N-[(S)-1-Carboxybutyl]-L-alanyl]-(1SR,3SR,5SR)-2-azabicyclo[3.3.0]-7-octene-3-carboxylic acid 0.5 g of the compound from Example 8 b is reacted in analogy to the procedure of Example 3.

Yield: 0.3 g (m/e: 306, MW—$H_2O$)

EXAMPLE 10

2-[N-[(S)-1-Ethoxycarbonyl-3-cyclohexylpropyl]-L-alanyl]-(1R,3S,5R)-2-azabicyclo[3.3.0]-7-octen-3-carboxylic acid

(a) tert.-Butyl 2-[N-[(S)--ethoxycarbonyl-3-cyclohexylpropyl]-alanyl]-(1R,3S,5R)-2-azabicyclo[3.3.0]-7-octen-3-carboxylate 1.0 g of the tert.-butyl ester from example 2d are reacted with 1.3 g of N-(1-S-ethoxycarbonyl-3-cyclohexylpropyl-L-alanine as described in Example 1e.

Yield: 2.0 g of a mixture of diastereomers which is separated by column chromatography on silica gel using petroleum ether/acetan 2:1 as an eluent.

Yield of the title compound: 0.9 g; $[\alpha]_D^{20}$: −98° (c=6, ethyl acetate).

The isomeric compound tert.-butyl 2-[N-[(S)-1-ethoxycarbonyl-3-cyclohexylpropyl]-L-alanyl]-(1S,3R,5S)-2-azabicyclo[3.3.0]-7-octen-3-carboxylate shows $[\alpha]_D^{20}$: +75° (c=5, ethyl acetate).

(b) 2-[N-[(S)-1-Ethoxycarbonyl-3-cyclohexylpropyl]-L-alanyl]-(1R,3S,5R)-2-azabicyclo[3.3.0]-7-octen-3-carboxylic acid 0.5 g of the compound from Example (10a) having the S,S,S,S,S configuration are reacted following the procedure of Example 1(h).

Yield: 0.2 g; $[\alpha]_D^{20}$: −84.6° (c=1, $CH_3OH$)

The isomeric compound having the S,R,S,S,S configuration, i.e. 2-[N-[(S)-1-ethoxycarbonyl-3-cyclohexylpropyl]-L-alanyl[-(1S,3R,5S)-2-azabicyclo[3.3.0]-7-octen-3-carboxylic acid, shows $[\alpha]_D^{20}$: +84° (c=3, $CH_3OH$).

EXAMPLE 11

2-[N-[(S)-1-Carboxy-3-cyclohexylpropyl]-L-alanyl]-(1R,3S,5R)-2-azabicyclo[3.3.0]-7-octen-3-carboxylic acid 0.1 g of the compound from Example (10b) (all S configuration) are reacted following the procedure of Example 3.

Yield: 0.6 g (m/e: 392).

We claim:

1. A compound of the formula I or a physiologically acceptable salt thereof

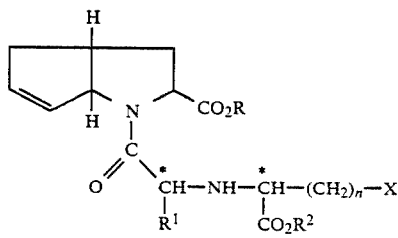

in which n denotes 0, 1 or 2,

R denotes hydrogen, ($C_1$ to $C_6$)-alkyl or aralkyl having 7 to 9 carbon atoms, $R^1$ denotes hydrogen or ($C_1$ to $C_6$)-alkyl which can optionally be substituted by amino, ($C_1$ to $C_4$)-acylamino or benzoylamino, ($C_2$ to $C_6$)-alkenyl, ($C_5$ to $C_9$)-cycloalkyl, ($C_5$ to $C_9$)-cycloalkenyl, ($C_5$ to $C_7$)-cycloalkyl-($C_1$ to $C_4$)-alkyl, aryl or partially hydrogenated aryl, each of which can be substituted by ($C_1$ to $C_4$)-alkyl, ($C_1$ or $C_2$)-alkoxy or halogen, aryl-($C_1$ to $C_4$)-alkyl or aroyl-$C_1$-alkyl, both of which can be substituted in the aryl radical as defined previously, or a side chain of a naturally occurring amino acid, $R^2$ denotes hydrogen, ($C_1$ to $C_6$)-alkyl, ($C_2$ to $C_6$)-alkenyl or aryl-($C_1$ to $C_4$)-alkyl, X denotes ($C_1$ to $C_6$)-alkyl, ($C_2$ to $C_6$)-alkenyl, ($C_5$ to $C_9$)-cycloalkyl, aryl which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkyl-amino or methylenedioxy, or 3-indolyl.

2. A compound of the formula I as claimed in claim 1, wherein the hydrogen atoms on the bridgehead carbon atoms 1 and 5 have the cis configuration with respect to one another.

3. A compound of the formula I or a salt thereof as claimed in claim 1, wherein the carbon atom in position 3 of the bicyclic system, and the carbon atoms in the side chain which are labeled with an asterisk, each have the S-configuration.

4. A compound of the formula I or a salt thereof as claimed in claim 1, wherein
n denotes 2, R denotes hydrogen or alkyl having 1 to 4 carbon atoms, $R^1$ denotes hydrogen, ($C_1$ to $C_3$)-alkyl, ($C_2$ or $C_3$) alkenyl, benzyl, phenethyl, 4-aminobutyl or benzoylmethyl, $R^2$ denotes hydrogen, ($C_1$ to $C_4$)-alkyl or benzyl and X denotes methyl, cyclohexyl, phenyl which can be monosubstituted or disubstituted or, in the case of methoxy, trisubstituted by ($C_1$ or $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)-alkylamino, nitro or methylenedioxy.

5. A compound of the formula I or a salt thereof as claimed in claim 1, wherein R denotes hydrogen, $R^1$ denotes methyl and X denotes phenyl, methyl or cyclohexyl.

6. A compound of the formula I or a salt thereof as claimed in claim 5, wherein $R^2$ denotes hydrogen or ethyl.

7. A compound of the formula I or a salt thereof as claimed in claim 6, wherein X denotes phenyl.

8. A compound of the formula I or a salt thereof as claimed in claim 2, wherein the carboxyl group on the carbon atom in position 3 of the bicyclic system has the endo orientation, and the abovementioned carbon atom and the carbon atoms in the side chain which are labeled with an asterisk each have the S-configuration, n denotes 2, R denotes hydrogen, $R^1$ denotes methyl, $R^2$ denotes ethyl, and X denotes phenyl.

9. A compound of the formula I or a salt thereof as claimed in claim 2, wherein the carboxyl group on the carbon atom in position 3 of the bicyclic system has the exo orientation, and the abovementioned carbon atom and the carbon atoms in the side chain which are labeled with an asterisk each have the S-configuration, n denotes 2, R denotes hydrogen, $R^1$ denotes methyl, $R^2$ denotes ethyl, and X denotes phenyl.

10. A compound of the formula III

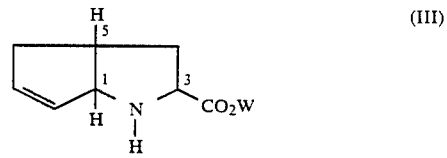

in which the hydrogen atoms on the carbon atoms 1 and 5 have the cis configuration in respect to one another, and the group —$CO_2W$ on carbon atom 3 is oriented exo or endo with respect to the bicyclic ring system, and in which W denotes hydrogen or a radical which can be eliminated with acid.

11. Method of treating high blood pressure which comprises administering an effective amount of a compound as or a salt thereof claimed in claim 1.

12. Pharmaceutical composition comprising an effective amount of a compound or a salt thereof as claimed in claim 1 and a pharmaceutically acceptable carrier.

* * * * *

UNITED STATES PATENT AND TRADEMARK OFFICE
CERTIFICATE OF CORRECTION

PATENT NO. : 4,920,144

DATED : April 24, 1990

INVENTOR(S) : Hansjorg Urbach et al.

It is certified that error appears in the above-identified patent and that said Letters Patent is hereby corrected as shown below:

Claim 1, Column 15, Line 46, "alkyl-amino" should be --alkylamino--;

Claim 8, Column 16, Line 25, "abovementioned" should be --above-mentioned--;

Claim 9, Column 16, Line 33, "abovementioned" should be --above-mentioned--;

Claim 11, Column 16, Line 55, "as or a salt thereof" should be --or a salt thereof as--;

Signed and Sealed this

Twenty-fifth Day of August, 1992

Attest:

DOUGLAS B. COMER

Attesting Officer

Acting Commissioner of Patents and Trademarks